(12) United States Patent
Balázs et al.

(10) Patent No.: US 6,269,997 B1
(45) Date of Patent: Aug. 7, 2001

(54) APPARATUS FOR ACTUATING A VARIETY OF INTERCHANGEABLE SURGICAL INSTRUMENTS FOR HOLLOW ORGAN ANASTOMOSIS

(75) Inventors: Matthias Balázs, Grafrath; Ulrich Hagn, Wessling, both of (DE)

(73) Assignee: Deutsches Zentrum-für Luft-und Raumfahrt e.V., Bonn (DE)

( * ) Notice: Subject to any disclaimer, the term of this patent is extended or adjusted under 35 U.S.C. 154(b) by 0 days.

(21) Appl. No.: 09/375,516

(22) Filed: Aug. 17, 1999

(30) Foreign Application Priority Data

Aug. 17, 1998 (DE) .............................. 198 37 258

(51) Int. Cl.⁷ ................................. A61B 17/068
(52) U.S. Cl. .................... 227/175.1; 227/176.1; 227/19
(58) Field of Search ................... 227/175.1, 19, 227/176.1, 179.1

(56) References Cited

U.S. PATENT DOCUMENTS

| | | | |
|---|---|---|---|
| 3,955,581 | * 5/1976 | Spasiano et al. | 227/175.1 |
| 4,319,576 | * 3/1982 | Rothfuss | 227/19 |
| 4,527,724 | * 7/1985 | Chow et al. | 227/19 |
| 4,573,468 | * 3/1986 | Conta et al. | 227/179.1 |
| 4,671,445 | 6/1987 | Barker et al. . | |
| 4,754,909 | * 7/1988 | Barker et al. | 227/19 |
| 4,903,697 | * 2/1990 | Resnick et al. | 227/19 |
| 5,093,208 | 3/1992 | Hayes et al. . | |
| 5,111,987 | * 5/1992 | Moeinzadeh et al. | 227/19 |
| 5,467,911 | * 11/1995 | Tsuruta et al. | 227/19 |
| 5,533,661 | 7/1996 | Main et al. . | |
| 5,588,580 | * 12/1996 | Paul et al. | 227/19 |
| 5,669,918 | 9/1997 | Balazs et al. . | |
| 5,685,474 | * 11/1997 | Seeber | 227/19 |
| 5,702,048 | * 12/1997 | Eberlin | 227/19 |
| 5,817,109 | * 10/1998 | McGarry et al. | 227/175.1 |
| 5,865,361 | * 2/1999 | Milliman et al. | 227/19 |

FOREIGN PATENT DOCUMENTS

| | | |
|---|---|---|
| 3818983 | 12/1988 | (DE) . |
| 9018151 | 12/1996 | (DE) . |
| 4091825 | 3/1992 | (JP) . |
| 7233456 | 9/1995 | (JP) . |

* cited by examiner

Primary Examiner—Scott A. Smith
(74) Attorney, Agent, or Firm—Browdy and Neimark

(57) ABSTRACT

For actuating a variety of interchangeable surgical instruments, more particularly for hollow organ anastomosis, an apparatus comprises at the proximal end of a shank part a handle part (2) secured releasably and correctly positioned thereto. A pivotable toggle mechanism is fitted to the handle part, the pivotable toggle mechanism cooperating releasably with the proximal end of a flexible, force-transmitting reciprocating part guidingly accommodated in the shank part. The proximal end of the reciprocating part is connected to an adjusting mechanism in the handle part. At the distal end of the reciprocating part a connector for connecting a surgical instrument is provided. At the distal end of the shank part a connector is provided for connecting a housing of the surgical instrument. Fitted to the distal end of the flexible reciprocating part is a pusher transmitting an axial compression force to the body of the surgical instrument.

18 Claims, 8 Drawing Sheets

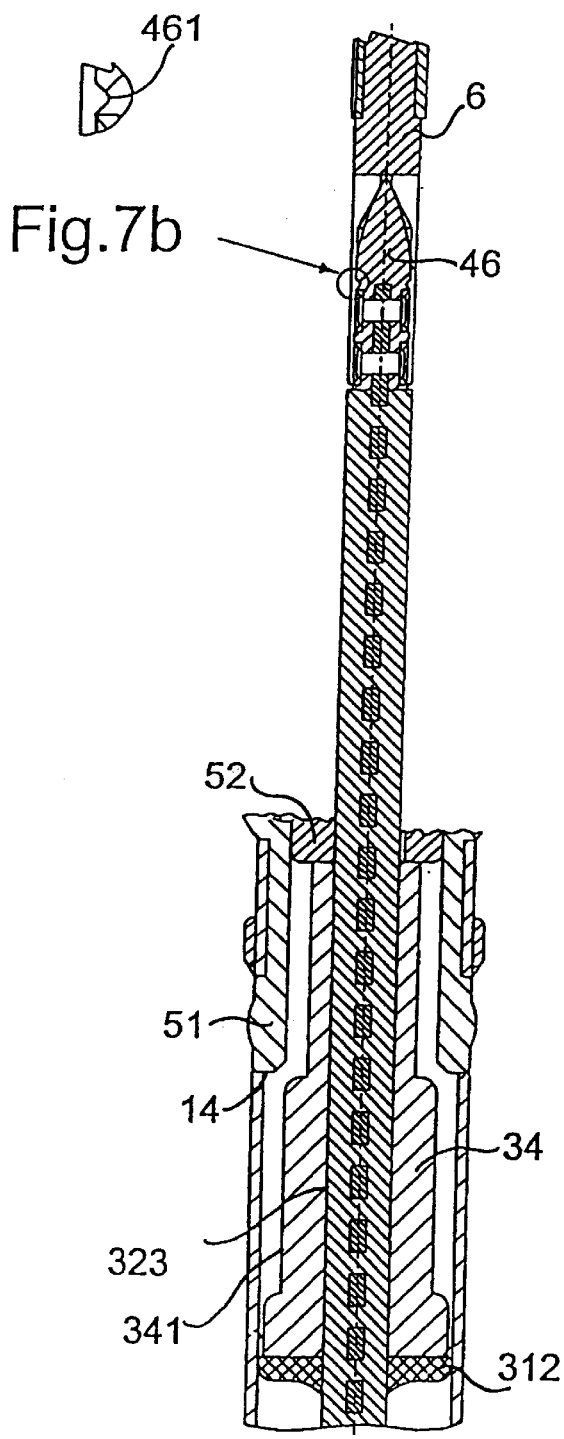
Fig.7a
Fig.7b
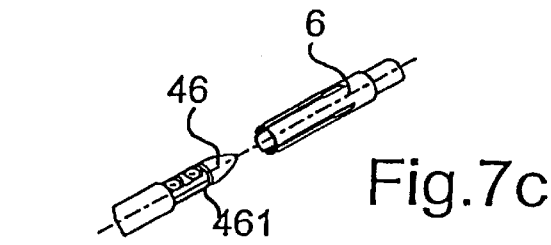
Fig.7c
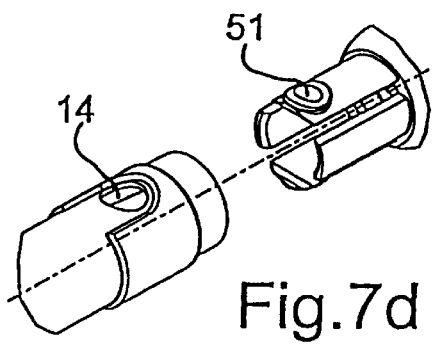
Fig.7d
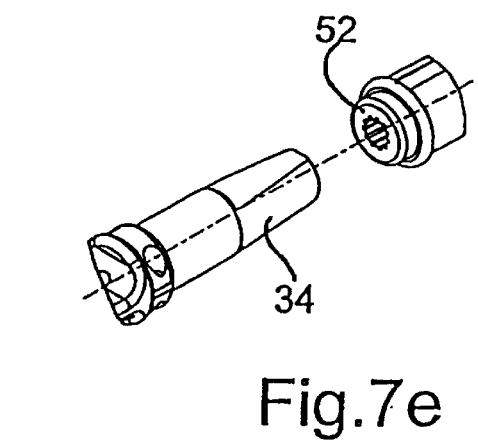
Fig.7e

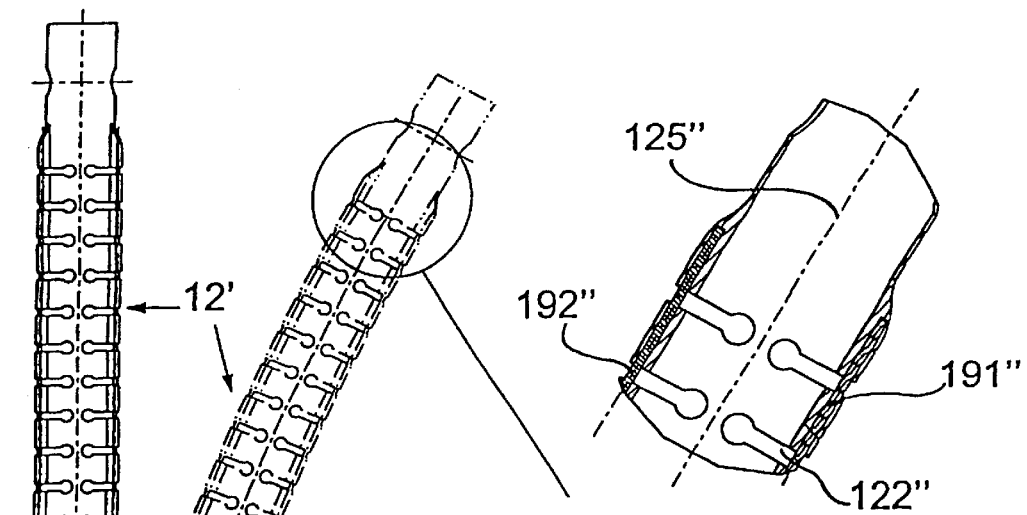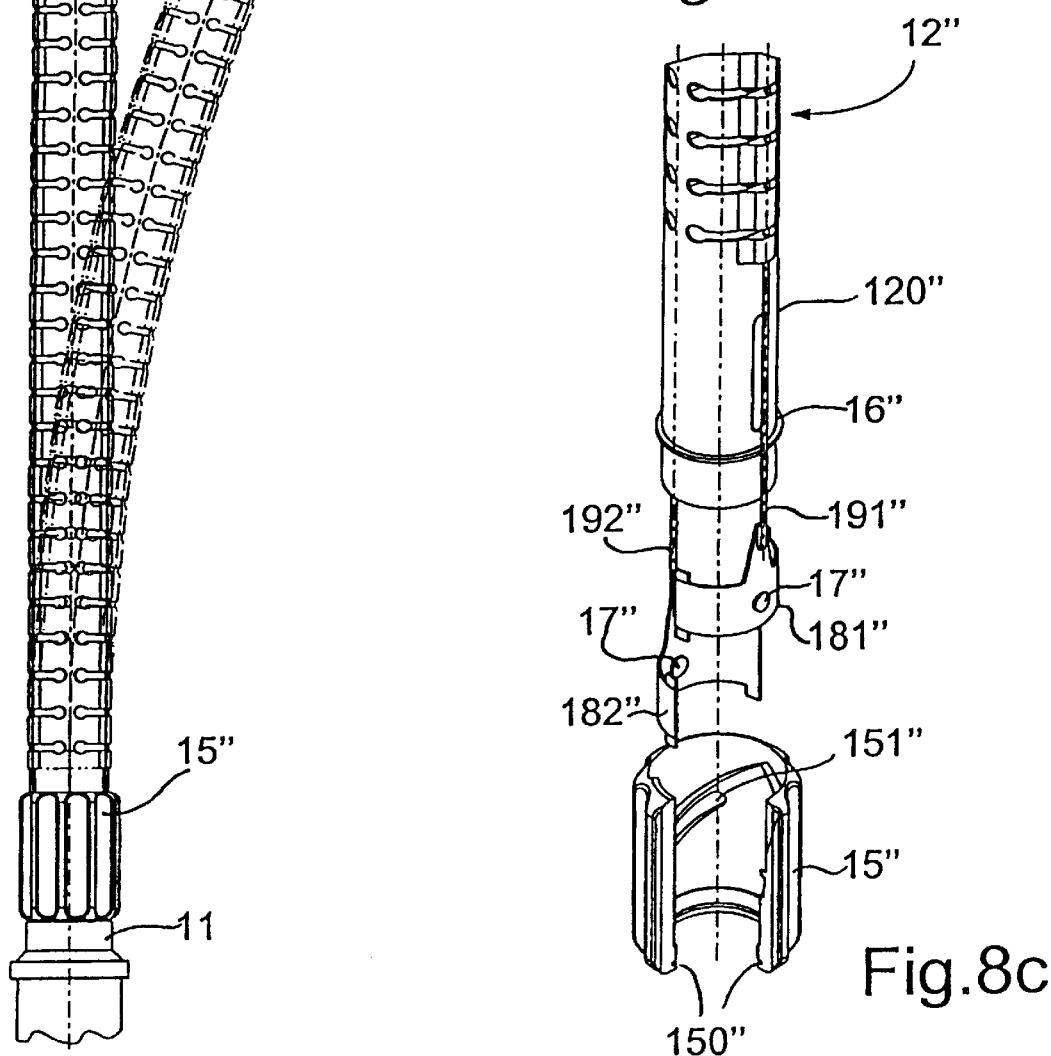

APPARATUS FOR ACTUATING A VARIETY OF INTERCHANGEABLE SURGICAL INSTRUMENTS FOR HOLLOW ORGAN ANASTOMOSIS

TECHNICAL FIELD AND BACKGROUND OF THE INVENTION

The invention relates to an apparatus for actuating a variety of interchangeable surgical instruments, more particularly for anastomosis (i.e parting, closing and connecting) of hollow organs.

Known from U.S. Pat. No. 4,573,468 is a surgical suture stapler including a reusable unit made up of a handle part and shank part as well as a mountable disposable head unit. This instrument comprises a pistol-type handle part and a straight shank part which cannot be separated from each other. The shank part is configured as a rigid, straight tube.

A mountable disposable head unit in the form of the suture stapler comprising suture staples, a staple ejector, a circular scalpel, a mandrel as well as an anvil is secured to the distal end of the shank part by means of a bayonet lock or a threaded connector.

Known from U.S. Pat. No. 5,533,661 is a suture stapler in which neither the shank nor the head is separable from the handle part and shank part respectively. Merely an anvil and a pin can be separated from the shank part. Furthermore the handle part cannot be disassembled and the whole instrument is devised exclusively for once-only use.

The known suture stapler, like other non-reusable surgical instruments, has various disadvantages which have proved to be nuisance in actual practice, although not each and every one of these instruments has all of the disadvantages as listed in the following, they usually having, however, several of these disadvantages at the same time.

The known instruments generally are too heavy, some of these instruments requiring for their actuation excessive operating forces and/or failing to incorporate feedback information means, for example, in the form of "stapling or cut performed". Non-reusable circular instruments involve high costs simply from the fact that they can only be used once and then need to be disposed of.

SUMMARY OF THE INVENTION

It is thus the object of the invention to design and implement an apparatus for actuating surgical instruments which is low-weight, requiring little force to operate and which more particularly is to be reused.

In an apparatus for actuating a variety of interchangeable surgical instruments in accordance with the invention a handle part is secured releasably and properly located to the proximal end of a shank part. Attached to the handle part is a pivotable toggle mechanism releasably in contact with the proximal end of a flexible, force-transmitting reciprocating part guidingly accommodated in the shank part. The proximal end of the reciprocating part is connected to an adjusting mechanism in the handle part. Connected to the distal end of the force-transmitting reciprocating part is a connector for producing a connection to a surgical instrument. Provided at the distal end of the reciprocating part is a push button fastener for attaching a housing of the surgical instrument whilst applied to the distal end of the flexible reciprocating part is a part transmitting an axial compressive force to the body of the surgical instrument.

In the apparatus of the invention the handle part may be disassembled for the purpose of cleaning/sterilization to advantage without requiring any tools. By means of a toggle mechanism provided on the handle part a higher force may be applied towards the end, for example, of a stapling action and excision so that a satisfactory tissue cut is reliably assured.

In the apparatus in accordance with the invention an adjusting mechanism permits to particular advantage a swift approximation, for example, of an anvil to a staple cartridge and in addition subsequently a vernier adjustment e.g. of a tissue gap. During approximation, i.e. movement of the anvil an axial adjustment is implemented which is transmitted via an internal pusher to an operating control on the handle part. For vernier adjustment a mechanism is provided which translates this axial movement into a rotary movement. This rotary movement is locked out during an operation, as a result of which the axial position of the adjusting mechanism is fixed in place.

Accordingly, in the apparatus in accordance with the invention the adjusting mechanism is automatically arrested in the vernier adjustment range and is thus unable to become displaced in performing the operation, for example, during a stapling action. A positive lock of the rotary movement enables very fine indexing of the vernier adjustment range to be achieved.

The shank part of the apparatus in accordance with the invention comprises a mechanism to transmit a predetermined force, for example. during a stapling action, as well as a predetermined travel, such as, for example, an adjustment travel for an anvil, whereby the force and the adjustment travel may be applied or implemented for both straight and single-axis bent shank tubes.

In apparatus in accordance with the invention comprises only two assemblies comprising a few elements suitable for reuse, simple to assemble locked in place and to disassemble, each of which is simple to clean and thus simple to resterilize. Via a push-button/mounting fastener designed for facilitated operation a variety of head units may be connected to the apparatus in accordance with the invention.

BRIEF DESCRIPTION OF THE DRAWINGS

The invention will now be detained by way of preferred embodiments with reference to the attached drawings in which:

FIG. 2a is a plan view, not true to scale, of a mechanism in the shank part as well as FIG. 2b is a magnified detail illustration of a partial portion of that as shown in FIG. 2a;

FIG. 7a is an axial section view through the end part of the shank part showing a connector for a mandrel and, for example, a staple cartridge;

FIG. 7b is a magnified illustration of a detail of the end part as shown in FIG. 7a;

FIG. 7c is an illustration in perspective of the end part of the shank part and a receiving mount for the mandrel, FIG. 7d is a magnified illustration in perspective of a push button fastener at the distal end of the shank part including a push button mechanism ssigned thereto at the proximal end of a staple cartridge;

FIG. 7e is an illustration showing a modified variant of the distal end of the shank part and one proximal end of a staple cartridge adapted thereto;

FIG. 8a illustrates a straight oriented, pliable shank tube, a shank tube bent to the right being indicated dashed:

FIG. 8b is a magnified section illustration of a detail of a distal shank tube end, and FIG. 8c is an exploded view in perspective illustrating the component parts for controlling the shank tube.

DETAILED DESCRIPTION

Figure 1:
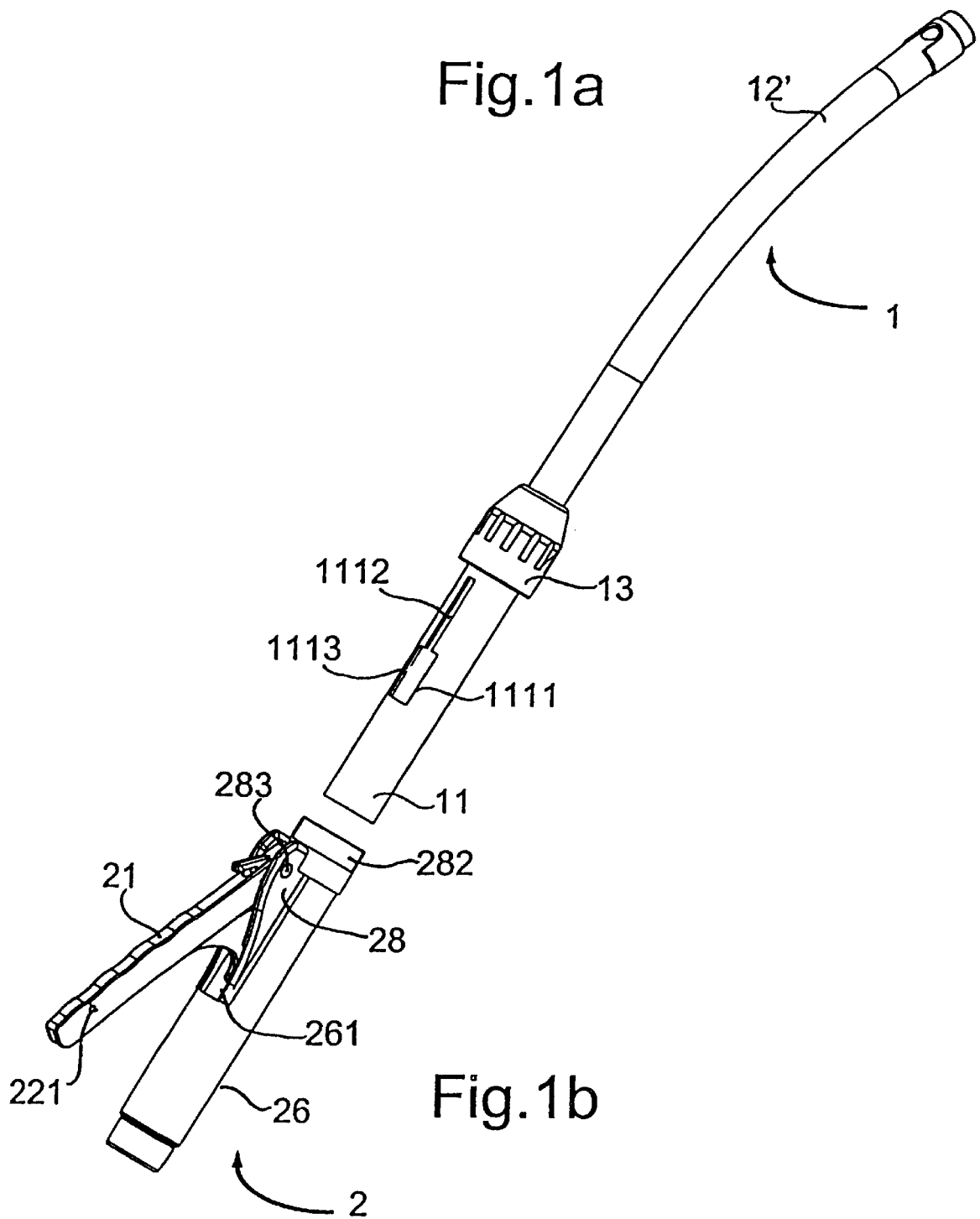
FIGS. 1a and 1b is each a schematic, perspective view of a preferred embodiment of a handle part as well as of a shank part released therefrom.
Figure 2:
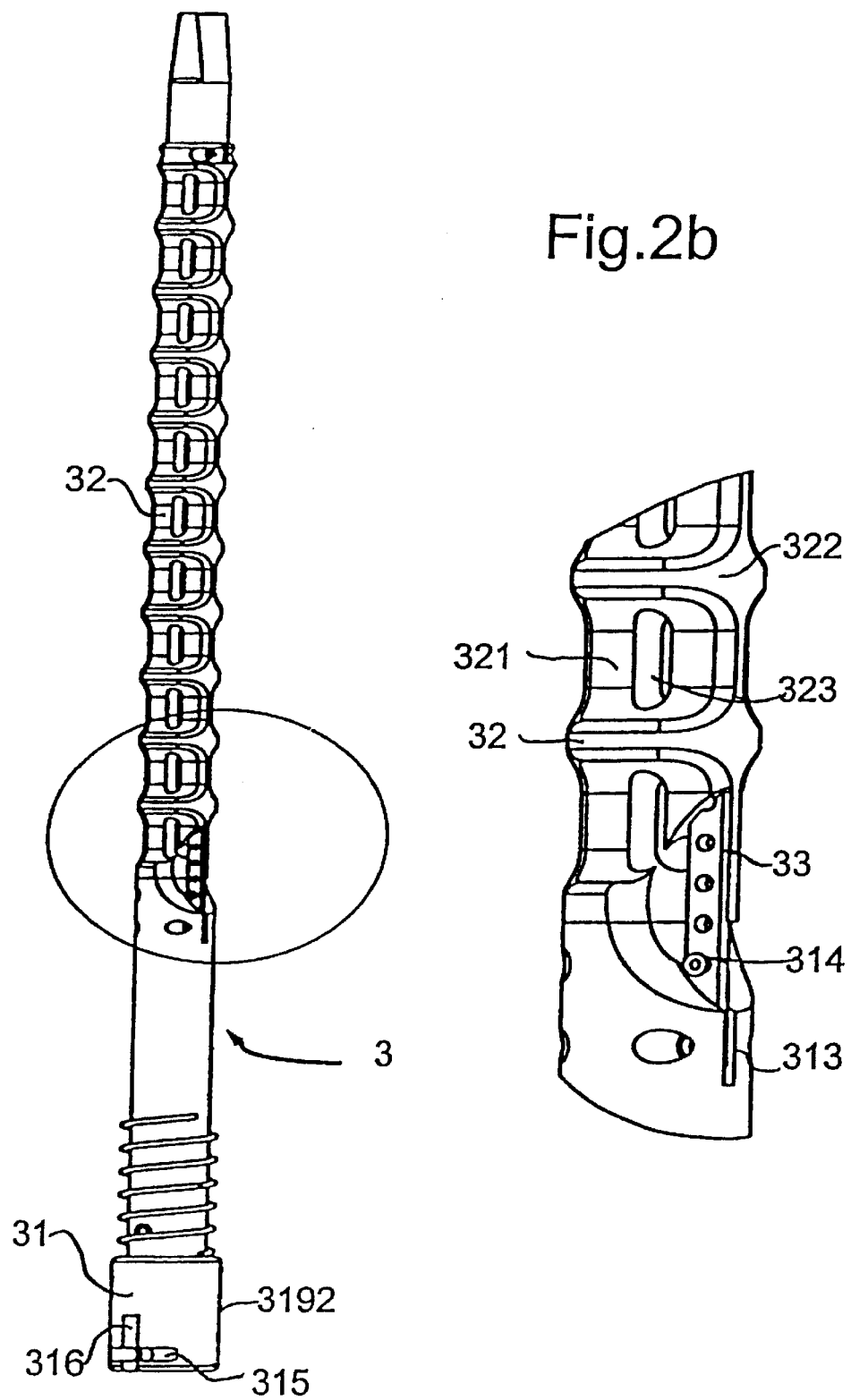
Figure 3:
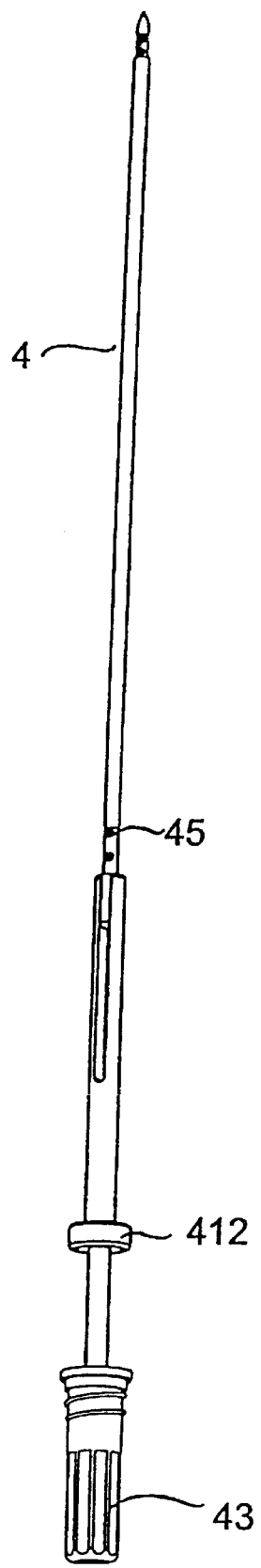
FIG. 3 is a schematic illustration of an adjusting mechanism.

Referring now FIGS. 1a to 3 there are illustrated partially in perspective the various assemblies, i.e. shank part assembly 1 (FIG. 1a), handle part assembly 2 (FIG. 1b), mechanism assembly 3 in the shank part 1 (FIGS. 2a and 2b) and adjusting mechanism assembly 4 (FIG. 3).

The following describes firstly the various elements of the handle part 2 as well as of the shank part 1. The handle part 2 comprises a tubular housing 26, a pivotable lever 21 as well as a leg 22; whereby lever 21 and leg 22 form together a toggle.

Figure 4:
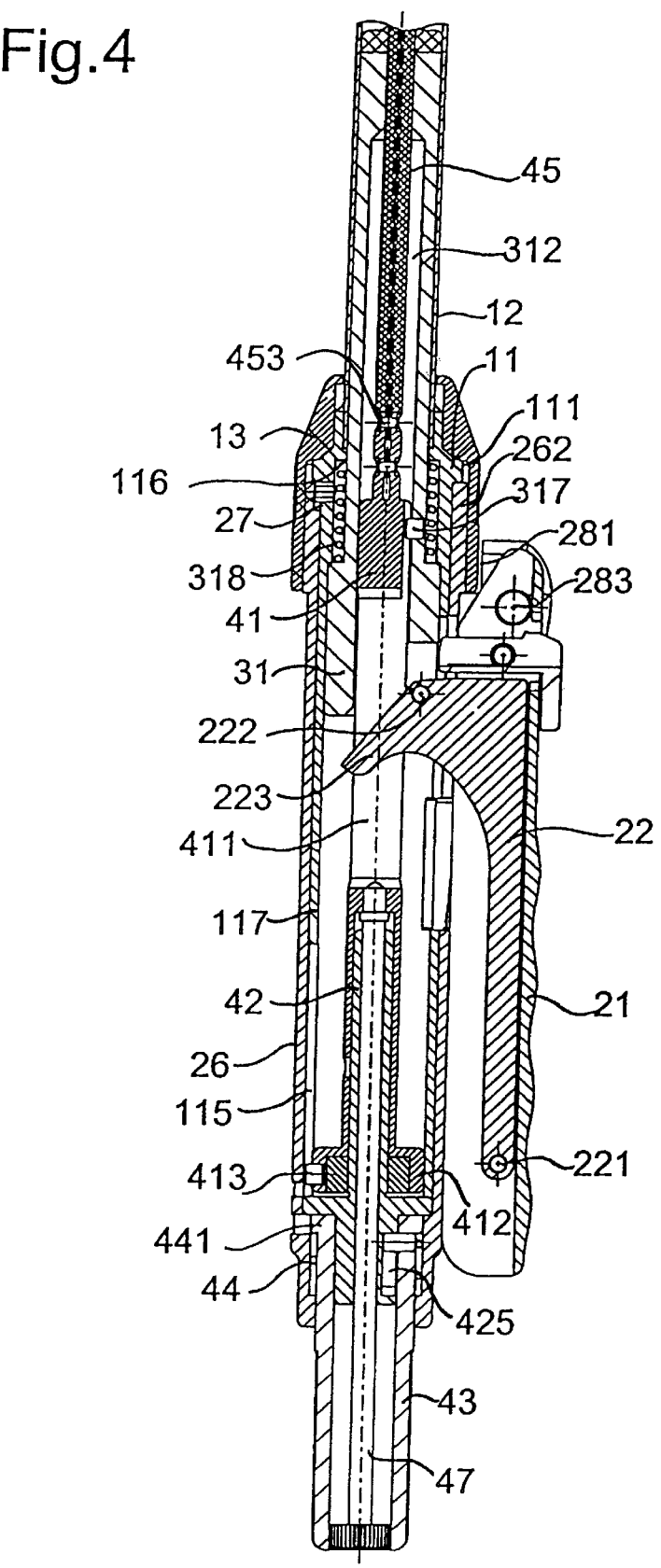
FIG. 4 is an axial section view of the handle part secured to the shank part with the operating control part actuated.
Figure 5:
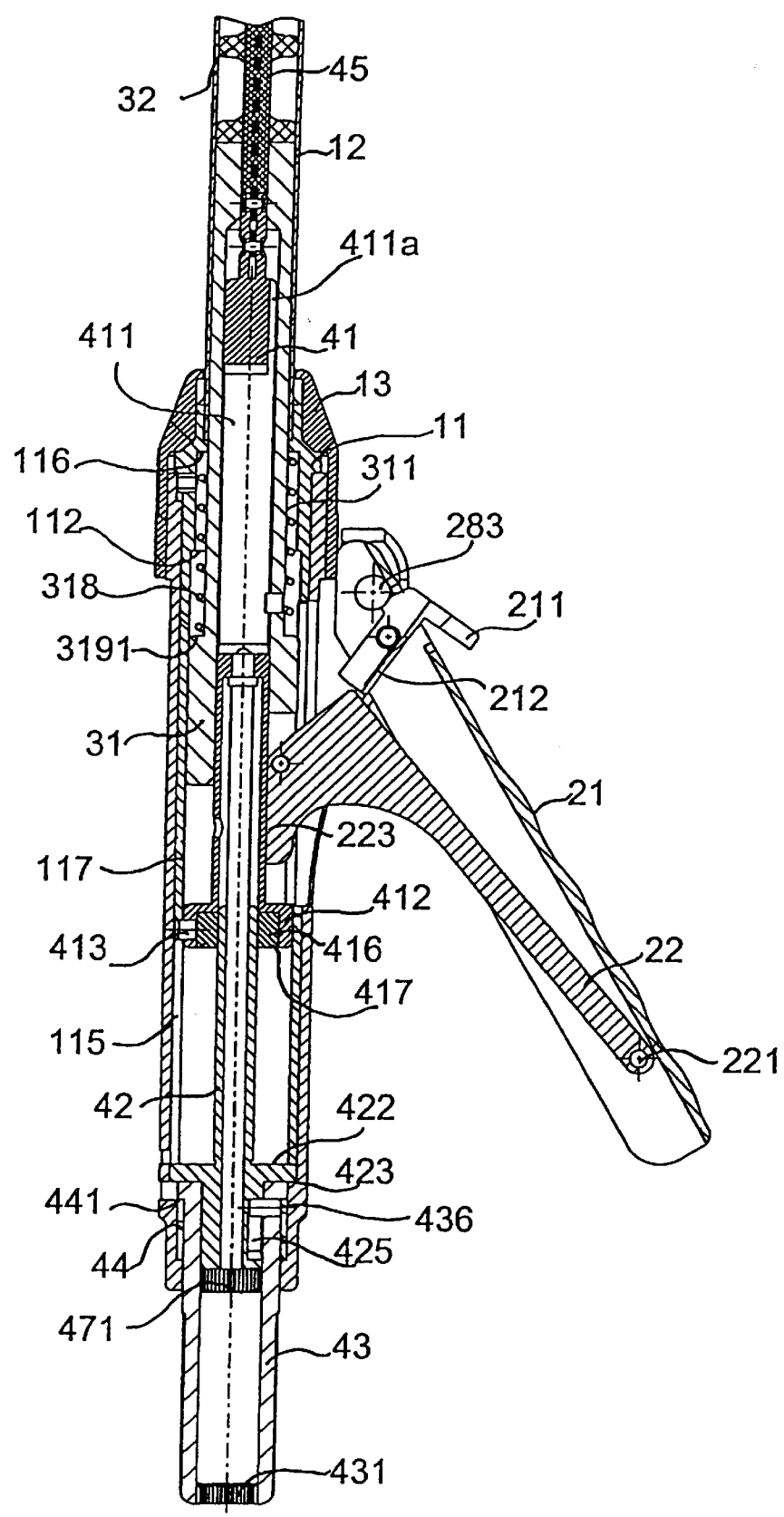
FIG. 5 is a axial section view, corresponding to that as shown in FIG. 4, of the handle part secured to the shank part with the operating control part non-actuated.
Figure 6:
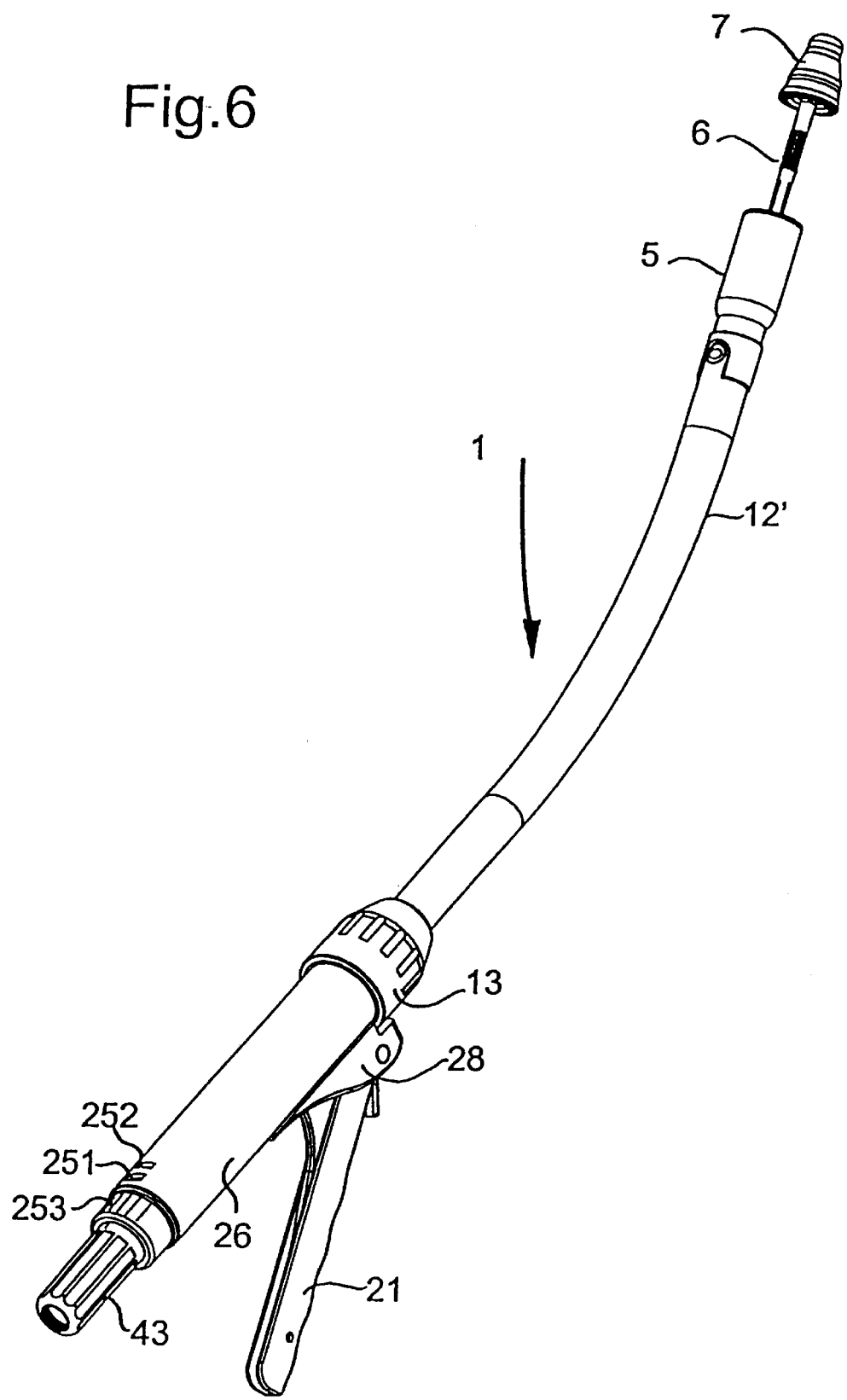
FIG. 6 is a perspective view of the handle and shank parts joined to each other and a fitted disposable head unit indicated schematically.

Referring now to FIG. 6 there is illustrated provided an indicator 252 configured as a window for verifying whether the adjusting mechanism 4 is in the vernier adjustment range, an indicator 251 for checking that the adjusting mechanism is arrested and a scale 253 for a set gap width. In addition an assembly groove 27 (see FIG. 4) is configured on the housing 26 to ensure proper location in fitting the shank part 1 to the distal end of the latter. The pivotable lever 21 is mounted pivotable by means of a pin 283 in two mounting pads 28. The leg 22 is movingly connected to the lever 21 via a pin 221 (FIGS. 4 and 5). At the end facing away from the pin 221 the leg 22 comprises a transverse pin 222 (FIG. 4) producing a connection to the mechanism assembly 3 via an intersection groove (FIG. 2a) formed by a transverse groove 315 and a longitudinal groove 316 to a connector 31 of flexible reciprocating part 32.

Referring now to FIGS. 1a and 1b there is illustrated that for assembly/disassembly the transverse pin 222 fixedly connected to the leg 22 is insertable and removable into/ from the transverse groove 315 through tee-shaped windows 261 and 1111 configured in the housing 26 of the handle part 2 and equivalently in a connector 11 of the shank part 1.

It is precisely then, when the toggle 21, 22 is fully open that the leg 22 may be inserted with its transverse pin 222 into the transverse groove 315 in the connector 31 through the tee-shaped windows 261, 1111. During operation a narrow portion 1112 of the tee-shaped window 1111 prevents the leg 22 from springing out of place from the connector 31.

During assembly/disassembly, toggle 21, 22 can only be opened further than as shown in FIG. 5 when as regards a cavity 281 (FIG. 4) a fastener nut 13 is not screwed onto a thread 262 of the housing 26, as a result of which in assembly/disassembly the toggle 21, 22 may be oriented so that the transverse pin 222 locates within a wide portion 1113 of the tee-shaped window 1111 thus enabling the toggle 21, 22 to be separated from the connector 31 of the flexible reciprocating part 32.

Via the pin 283 the lever 21 is movably or pivotably connected to the mounting pads 28 of the housing 26 between which lever 21 and leg 22 of the toggle can thus be moved. At the same time due to the configuration of the mounting pads 28 of lever 21 and leg 22 there is no risk of gripping occurring accidentally between lever 21 and leg 22.

Integrated in the lever 21 is a lock 211 (see FIG. 5) preventing unwanted actuation of the toggle, a leg spring 212 relatching the lock 211, for example, following implementation of a stapling action and having achieved the toggle position as shown in FIG. 5, The shank part assembly 1 is fixedly connected to the proximal (i.e. facing the operator) end in the handle part assembly 2 and at the distal (i.e. facing away from the operator) end a staple cartridge 5 indicated merely schematically in FIG. 6 and not described in detail, for example, may be applied by snap-action noses 51 provided at the proximal end thereof of a push button mechanism via a push button fastener 14 as is evident from FIG. 7d on a magnified scale.

The shank part assembly 1 may comprise a pliable, bent shank tube 12' (FIGS. 1a and 6) or also a straight, rigid shank tube 12 (FIGS. 4 and 5) and has furthermore a connector 11 connected to the corresponding shank tube 12 or 12' as well as the fastener nut 13 freely rotatable on the latter. The connector 11 comprises a stop 111 (FIG. 4) for both the nut 12 and housing 26.

For guiding and rotatively locking in place a middle part 41 of the adjusting mechanism 4 by means of a pin 413 protruding from the latter a longitudinal groove 115 is provided in the shank part 1. In a tubular runway 117 the middle part 41 is coaxially guided by a circular-cylindrical raised face 412 (FIG. 5) and the connector 31 by a circular-cylindrical section 3192 (FIG. 2a).

The mechanism assembly 3 provided for transmitting a force and an axial movement along the shank tube 12 consists in all of three main components: the connector 31 accommodated mainly in the handle part 2, the flexible reciprocating part 32 and two thin metal bodies 33 embedded in the latter (FIG. 2b) which due to their axial stiffness transmit an axial force. The flexible reciprocating part 32 guides the metal bodies 33 along the neutral fiber whilst permitting bending in a single axis due to its shell surface area comprising recesses 321 and circular-cylindrical sections 322.

The force is transmitted at the distal end of the mechanism assembly 3 by a graduated pusher 34 (FIGS. 7a and 7e) as an axial compressive force to a corresponding component in a staple cartridge 5, for example. At its distal end the pusher 34 comprises a section 341 having a corresponding large diameter so that in executing, for example, a stapling action the snap-action noses 51 of the push button fastener 14 (see FIG. 7d) are locked in place to prevent accidental opening by the forward displacement of the pusher 34 and the flexible reciprocating part 32 in connection therewith distally. The mechanism assembly 3 is configured tubular throughout and comprises a preferably central working passage 312 or 323 (guided along the neutral fiber) in which part of the adjusting mechanism 4 is movingly guided.

Guided on the cylindrical outer surface area 311 of the connector 31 is a spring 318 (FIGS. 4 and 5). The mechanism assembly 3 and adjusting mechanism assembly 4 are mutually oriented rotatively by a dowel pin 317 (FIG. 4) and a groove 411a (FIG. 5). The complete mechanism assembly 3 is pretensioned against an annular stopping surface area 116 by means of the spring 318 so that the toggle 21, 22 can be returned to the starting position as shown in FIG. 5 after implementation of a stapling action, for example.

For moving the mechanism assembly 3 relative to the shank part assembly 1 and handle part assembly 2 the transverse pin 222 of the leg 22 engages the transverse groove 315 in the connector 31, as a result of which the axial force produced by the toggle 21, 22 is transmitted to the mechanism assembly 3.

Sliding in the spacious working passage 312 is the middle part 41. A stopping surface area 3191 of the connector 31 forms with a stopping surface area 112 of the connector 11 the travel limit of the mechanism 3. A groove 313 (FIG. 2b) receives the force-transmitting metal bodies 33 which is fixedly connected to the connector 31 by rivets 314. The metal bodies 33 are embedded in the flexible reciprocating part 32 and are thus guided along the neutral fiber of the shank tube 12.

The flexible reciprocating part 32 comprises the working passage 323, preferably arranged centrally, recesses 321 permitting flexing of the flexible reciprocating part 32 in complying with the bending of the shank tube, and circular-cylindrical sections 322 serving, on the one hand, guidance in both a straight and curved shank tube and, on the other, to prevent kinking of the metal bodies 33. A good connection to the flexible reciprocating part 32 is assured by the perforation of the metal bodies 33.

It is also possible to do away with the metal bodies 33 and to transmit a force exclusively via the flexible reciprocating part 32. Preferably, further working passageways may be optionally incorporated in the flexible reciprocating part 32 along the neutral fiber of the curved shank tube 12 to provide the mechanism with additional functions, where necessary.

The adjusting mechanism 4 provides the operator with an operating control on the handle part 2 with the aid of which, for example, an anvil 7 may be retracted and extended. Mounted in the handle part 2 is a spindle 42 rotatively movable but axially defined by stops 422 and 423 relative to the connector 11 and the housing 26. The spindle 42 is screwed into a threaded insert 416 of the middle part 41.

Via rivets 453 a core 45, acting as the thrust driving medium, is connected to the middle part 41, this core comprising a force-transmitting metal body embedded in a flexible cylindrical body, preferably made of a plastics material, for guiding and protective purposes. By means of the core 45 the adjustment travel is transmitted from the handle part 2 along the shank tube 12 via the circumferential groove 461 (FIG. 7b) at joint 46, for example, to a mandrel 6 and the anvil 7.

The middle part 41 is rotatively defined by the pin 413 and the groove 115 relative to the joint 11. The operating moment for the adjusting mechanism 4 is transmitted from a handwheel 43 via a pin 436 and a groove 425 to the spindle 43. Pin 436 and groove 425 permit the handwheel 43 to be axially shifted by a predetermined travel relative to the spindle 42. This movement is counteracted by a compression spring 44 (indicated merely by a winding) supported by the housing 26. Turning the handwheel 43 produces a translatory movement of the middle part 41 as a result of which an anvil, for example, is adjusted.

In the last proximity portion of, for example, the anvil 7 relative to the staple cartridge S the pin 413 becomes visible in the indicator window 252 (FIG. 6) indicating, "STAPLE ON", for example. A serration 471 of a latch 47 fixedly connected to the middle part 41 mates with the serration 431 of the handwheel 43, therefore resulting in the adjusting mechanism 4 and thus, for example, the anvil adjustment being locked.

For a further adjustment the handwheel 43 needs to be pulled out from the housing 26 against the force of the compression spring 43 so that the serrations 431 and 471 no longer mate, the handwheel 43 then permitting further turning and, for example, a corresponding gap width setting via the scale 253 (FIG. 6). As soon as a desired gap width has been set, the handwheel can be released which will then snap back into place in the housing as urged by the compression spring 44. The serrations 431 and 471 then re-arrest the adjusting mechanism 4 and a raised face 441 on the handwheel 43 is only to be seen in the housing window 251 when arresting has been done correctly (FIG. 6).

The adjustment travel is defined by the stopping surface areas 422 and 417 as well as by the length of the groove 115. It is not until the adjusting mechanism is in the vernier adjustment range that the toggle 21, 22 can be operated, i.e. it not being until then that a stop 223 of the leg 22 is able to pivot through a slot 411 in the middle part 41.

For connecting a head unit, for example a circular suture stapler, to the shank part 1 of the apparatus in accordance with the invention the following individual fasteners are provided:

1. The push button fastener 14 (FIG. 7d) connects the housing of a head unit via push buttons 51 seated on spring tabs with the shank tube 12 of the shank part 1, the push buttons 51 engaging corresponding radial holes in the shank tube 12 of the shank part 1.

2. A mountable connector 46 connects a body 6 of the head unit to the adjusting mechanism 4, a circular raised face on the inner contour of the slotted tubular end of the body 6 engaging a corresponding circumferential groove 461 on the connector 46.

Once the mandrel has been mounted on the connector 46 and travelled towards the instrument, locking to prevent accidental release occurs by the graduated pusher 34 preventing radial opening of the connection on the mandrel 6 by a corresponding fit.

3. The graduated pusher 34 transmits the operating force as an axial compressive force to the body 52 of the head unit.

Referring now to FIG. 8a there is illustrated a shank tube 12" controllably deflectable in a single plane, i.e. from a straight position as indicated by the bold line into a deflected position on the right as indicated by the broken line. The shank tube 12" as shown in FIG. 8a may be fitted instead of an e.g. rigid, straight shank tube 12 as shown in FIGS. 4 and 5 to the handle part 2 which otherwise remains unchanged.

Making the adjustment into a deflected position is implementable, for example, by means of a rotating ring 15" provided at the proximal end of the shank tube 12", this rotating ring being integrated directly upstream of a nut 13 (not shown in FIG. 8a) on the connector 11" and thus in the shank part, with no change to the handle part assembly.

The rotating ring 15" is guided in a groove 150" configured therein axially on an annular raised face 16" of the shank tube 12 and comprises on the inside two opposing coupling links 151" engaging noses 17" protruding from the connectors 181", 182" and configured preferably cylindrical. The connectors 181", 182" are rotatively defined by noses 17" and straight axial grooves 121".

Turning the rotary grip 15" moves the one connector 181" proximally and the other connector 182" distally; both connectors 181", 182" then covering the same distance in the opposite direction relative to the lower end 120" of the shank tube 12". It is due to this arrangement that the flexible shank tube 12" is deformed elastically into more or less a circular arc in a portion in which indentations 122" more or less optionally pliable are provided between webs 123". In this arrangement the neutral fiber 125" as indicated dot-dashed in FIG. 8b maintains a constant length.

Further evident from FIG. 8c are tractive driver means 191" and 192" secured at their proximal ends to the connectors 181" and 182" respectively and at their distal ends diametrally opposing the proximal end of the flexible shank tube 12" (see FIG. 8b).

A sheath (not shown in FIGS. 8a to 8c) of the shank tube 12" in the form of a tubing, for example, serves to cover the indentations 122' of the shank tube to thus create a shank tube 12" which is smooth inside and out.

The rotating ring 15" is configured self-locking to safeguard against accidental rotation and thus a deflection of the shank tube 2" (not shown in FIG. 8c) or it is provided with a breakaway lock (likewise not shown). To facilitate assembly the grooves 151" configured skew in the rotating ring 15" and serving as coupling links comprise a preferably axial groove orientation (not shown in FIG. 8c).

List of Reference Numerals 1 shank part assembly
11 connector
111 stop for 13 and 26
112 surface area of 11
1111 tee-shaped window in 11
1112 narrow portion
1113 wide portion
115 longitudinal groove
116 annular stopping surface area
117 tubular runway
12 straight shank tube
12' shank tube bent in a single axis
12" flexible shank tube
120" end of 12"
122' indentation
123' web
13 fastener nut
14 push button fastener for 5
15" rotating ring
150" groove
151" groove
16" annular raised face
17" noses
181" connector
182" connector
191" tractive driver means
192" tractive driver means
2 handle part assembly
21 lever
211 lock
212 leg spring
22 leg
221 pin
222 connector
223 stop
251 adjusting mechanism checking indicator
252 window indicating "vernier adjustment range"
253 gap width scale
26 housing
261 tee-shaped window in 26
262 thread
27 assembly groove
28 mounting pads
281 cavity
282 thread
283 pin
3 mechanism assembly
31 connector for 32
311 cylindrical surface area of 31
312 working passage
313 groove
314 rivets
315 transverse groove
316 longitudinal groove
317 dowel pin
318 spring
3191 stopping surface area on 31
3192 cylindrical section of 31
32 flexible reciprocating part
321 recesses in 32
322 cylindrical sections of 32
323 working passage
33 force-transmitting metal bodies
34 graduated pusher
341 section of 34
4 adjusting mechanism assembly
41 middle part of 4
411 slot in 41
411a groove
412 cylindrical raised face
413 pin
416 threaded insert
417 face surface area
42 spindle
422 surface area
423 stop
425 groove
43 handwheel
431 serration
436 pin
44 compression spring
441 raised face
45 core
453 rivets
46 joint
461 transverse groove in 46
47 latch
471 serration on latch 47
5 staple cartridge
51 snap-action nose
52 body
6 mandrel
7 clincher insertion head

What is claimed is:

1. An apparatus for actuating a variety of interchangeable surgical instruments, more particularly for hollow organ anastomosis wherein
    at the proximal end of a shank part (1) a handle part (2) is secured releasably and correctly positioned,
    a pivotable toggle mechanism (21, 22) is fitted to said handle part (2), said pivotable toggle mechanism (21, 22) cooperating releasably with the proximal end of a flexible, force-transmitting reciprocating part (32,45) guidingly accommodated in said shank part (1), the proximal end of said reciprocating part (32, 45) being connected to an adjusting mechanism (4) in said handle part (2),
    at the distal end of said reciprocating part (32, 45) a connector (46) for connecting a surgical instrument is provided,
    at the distal end of said shank part (1) a connector (14) is provided for connecting a housing of said surgical instrument,
    fitted to the distal end of said flexible reciprocating part (32) is a pusher (34) transmitting an axial compression force to the body of said surgical instrument, said force-transmitting reciprocating part comprises first and second components, said first component being coupled to said adjusting mechanism for operating said adjusting mechanism and said second component being coupled to the body of the surgical instrument and being operable for transmitting the axial compression force to the body of the surgical instrument, said first component and second component are movable independently of one another, said toggle mechanism comprises a lever (21) pivotably mounted between mounting pads (28) and a leg (22) movably connected to said lever (21), said leg (22) cooperating releasably for transmitting an axial force produced by means of said lever (21) to the proximal end of said flexible reciprocating part (32), and for releasably mounting said leg (22) in said flexible reciprocating part (32), an intersecting groove (315, 316) comprising a transverse and longitudinal groove is provided in said connector (31) applied to the proximal end of said flexible reciprocating part (32), correspondingly configured tee-shaped windows (261 or 1111) being assigned to said intersecting groove (315, 316) in said handle housing (26) and in a connector (11) provided at the proximal end of said shank part (1).

2. The apparatus as set forth in claim 1 wherein to safeguard against accidental actuation of said toggle mechanism a lock (211) is integrated in said lever (21) thereof.

3. The apparatus as set forth in claim 1 wherein for securing said shank part (1) to said handle part (2) a fastener nut (13) is accommodated freely rotatable on said connector (11) fixedly connected to the proximal end of said shank part (1) and said connector (11) comprising a stop (111) common to both said fastener nut (13) and to said handle housing (26).

4. The apparatus as set forth in claim 1 wherein an indicator (222) for indicating the position of said adjusting mechanism (4) in the free adjustment range, an-indicator (251) for checking that said adjusting mechanism (4) is arrested and a scale (253) for indicating the adjustment width of a gap are provided on said tubular handle housing (26).

5. The apparatus as set forth in claim 1 wherein the middle part (41) of said adjusting mechanism (4) is guided in said shank part (1) locked in place rotatively.

6. The apparatus as set forth in claim 5 wherein said middle part (41) is guided locking in place rotatively by a pin (413) protruding therefrom in a longitudinal groove (115) of said shank part (1) and is coaxially guided in said handle housing (26) by a circular-cylindrical raised face (412).

7. The apparatus as set forth in claim 1 wherein for transmitting an axially oriented force along said shank tube (12;12') said connector (31) coaxially guided in said handle part (2) is fixedly connected to said flexible reciprocating part (32) by two stiff bodies embedded therein (32).

8. The apparatus as set forth in claim 7 wherein said stiff bodies are metal bodies (33).

9. The apparatus as set forth in claim 1 wherein said first component of said force-transmitting reciprocal part comprises a core (45) connected to said adjusting mechanism (4) and accommodated in a preferably centrally arranged working passage (312, 3223) of said flexible reciprocating part (32).

10. The apparatus as set forth in claim 1 wherein for limiting the travel of said axial shiftable reciprocating part (32) a stop (3191) is configured on said connector (31) as well as a stop (112) on said connector (111).

11. The apparatus as set forth in claim 1 wherein said flexible reciprocating part (32) comprises alternating recesses (321) and circular-cylindrical sections (322) for guiding in a straight or bent shank tube (12 or 12').

12. The apparatus as set forth in claim 1 wherein said first component of said force-transmitting reciprocal component comprises a core(45), and for shifting said core (45), said middle part (41) of said adjusting mechanism (4) is secured to the proximal end of said core, said adjusting mechanism (4) being shiftable by means of a spindle (42) rotatively movable in a limited range and axially guided in said handle part.

13. The apparatus as set forth in claim 1 wherein for transmitting an adjustment movement a handwheel (43) is provided as an operating control element in said adjusting mechanism (4) cooperating with said spindle (42).

14. The apparatus as set forth in claim 13 wherein for transmitting an operating control moment from said handwheel (43) to said spindle (42) a pin (436) engaging a groove (425) is provided.

15. The apparatus as set forth in claim 1 wherein said adjusting mechanism (4) for adjusting said required gap width is arrested by an inner serration (431) of said handwheel (43) being springingly maintained mated with the outer serration (471) of a latch (47) connected to said middle part (41).

16. The apparatus as set forth in claim 1 wherein said connector for connecting a surgical instrument to the distal end of said shank part (1) is configured as a push button fastener (14) with push buttons (51) provided on flexible tabs.

17. The apparatus as set forth in claim 1 wherein for deflecting a flexible shank tube (12") tractive driver means (191", 192") are secured to the proximal end thereof diametrally opposed, the opposite ends of which are secured to connectors (181", 182") guided in a rotary hollow ring (15") so that rotation of said hollow ring (15") shifts said connectors (181", 182") by the same amount in the opposite direction.

18. The apparatus as set forth in claim 17 wherein guide links (151") having a constant or variable ramp are configured in said hollow ring (15"), protruding noses (17") being received by semi-circular connectors (181", 182") in said guide links.

* * * * *